United States Patent [19]

Denoya et al.

[11] Patent Number: 5,776,735

[45] Date of Patent: Jul. 7, 1998

[54] PROCESS FOR DIENONE MACROLIDES

[75] Inventors: Claudio D. Denoya. Groton; Edmund W. Hafner. East Lyme; Hamish A. I. McArthur. Gales Ferry, all of Conn.

[73] Assignee: Pfizer Inc., New York, N.Y.

[21] Appl. No.: 744,474

[22] Filed: Nov. 6, 1996

Related U.S. Application Data

[60] Provisional application No. 60/008,251, Dec. 4, 1995.

[51] Int. Cl.[6] .......................... C12P 19/62; C12N 15/00; C12N 1/20; C07H 17/08
[52] U.S. Cl. ................. 435/76; 435/172.3; 435/252.1; 536/7.1
[58] Field of Search ..................... 435/76, 172.3, 435/252.1; 536/7.1

[56] References Cited

U.S. PATENT DOCUMENTS

| | | | |
|---|---|---|---|
| 3,975,372 | 8/1976 | Ganguly et al. | 536/7.1 |
| 4,357,325 | 11/1982 | Ose et al. | 514/30 |

OTHER PUBLICATIONS

Puar et al., Journal of Antibiotics, 43, 1497–1501, (1990).
Wagman et al., Journal of Antibiotics, 25, 641–646, (1972).
Fukagawa et al., Journal of Antibiotics, 37, 118–126, (1984).

*Primary Examiner*—Nancy Degen
*Assistant Examiner*—John S. Brusca

*Attorney, Agent, or Firm*—Peter C. Richardson; Gregg C. Benson; Robert T. Ronau

[57] ABSTRACT

The process of this invention is directed to isolating or otherwise obtaining an olefinic macrolide producing microorganism which microorganism does not contain epoxidase enzyme activity. This invention also relates to a process for preparing said olefinic macrolide by fermenting a mutant microorganism lacking epoxidase activity, designated rosX herein, which mutant is obtained from the wild-type microorganism. This invention also relates to a rosX mutant of *Micromonospora rosaria*, and to any microorganism having the identifying characteristics thereof, said mutant also designated ATCC 55709. This invention also relates to a process for preparing repromicin, the compound of formula (II).

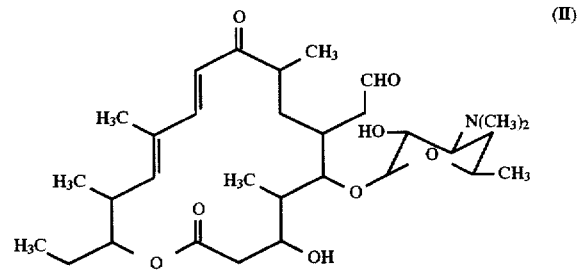

(II)

by mutating a wild-type microorganism capable of producing rosamicin to produce a mutant microorganism lacking epoxidase activity such that repromicin is produced by said mutant microorganism.

22 Claims, No Drawings

PROCESS FOR DIENONE MACROLIDES

This application claims the benefit of U.S. Provisional Application Ser. No. 60/008,251, filed Dec. 4, 1995.

BACKGROUND OF THE INVENTION

This invention relates to a process for isolating or otherwise obtaining an olefinic macrolide producing microorganism which microorganism does not contain epoxidase enzyme activity. This invention also relates to a process for preparing said olefinic macrolide by fermenting a mutant microorganism lacking epoxidase activity, designated rosX herein, which mutant is obtained from the wild-type microorganism. This invention also relates to a rosX mutant of *Micromonospora rosaria*, and to any microorganism having the identifying characteristics thereof, said mutant also designated ATCC 55709.

Rosamicin, the compound of formula (I)

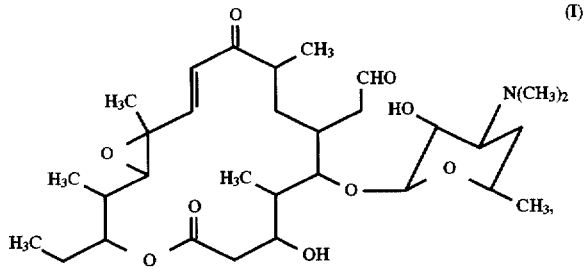

is an antibacterial macrolide produced by fermenting *Micromonospora rosadia*, ATCC 55708.

It is now known that the immediate precursor to rosamicin in the biosynthesis thereof is repromicin, the compound of formula (II). Repromicin

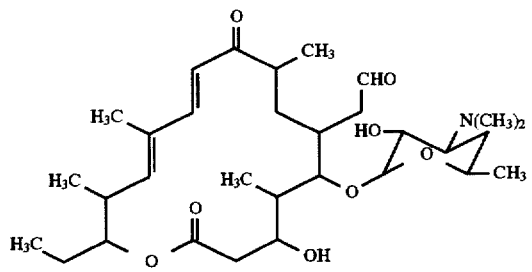

differs structurally from rosamicin in only one way: repromicin has a double bond at the C-12/C-13 position whereas rosamicin has an epoxide. Repromicin cannot be isolated directly from fermentation broths produced by wild type *Micromonospora rosaria* in significant amounts because the microorganism has an epoxidase enzyme responsible for epoxidating the C-12, C-13 olefin of repromicin to form the C-12, C-13 epoxide of rosamicin.

Repromicin is prepared chemically by the deepoxidation of rosamicin. The reaction suffers from very low yields. A high-yield process for the preparation of repromicin is desirable, since repromicin is a well known key intermediate in the synthesis of various antibiotics having the same or similar ring structure as repromicin.

The instant invention discloses that repromicin can be prepared by fermenting a rosX mutant of *Micromonospora rosaria*, and particularly from the rosX mutant of *Micromonospora rosada* which is designated ATCC 55709, and by isolating repromicin from the fermentation broth. A rosX mutant of *Micromonospora rosaria* does not contain epoxidase enzyme activity which is found in the wild type *Micromonospora rosaria*. As such, said mutant is incapable of producing the epoxidated macrolide rosamicin.

SUMMARY OF THE INVENTION

The present invention is directed to a process for preparing a microorganism capable of producing an olefinic macrolide comprising inactivating an epoxidase activity of a wild-type epoxy macrolide producing microorganism.

The present invention is particularly directed to a process as described in the preceding paragraph wherein said olefinic macrolide is a dienone macrolide.

The present invention is further directed to a process for preparing a microorganism capable of producing an olefinic macrolide comprising inactivating epoxidase activity of a wild-type epoxy macrolide producing microorganism and further comprising isolating a gene coding for said epoxidase activity from said wild-type epoxy macrolide producing microorganism and inactivating said gene.

The present invention is particularly directed to a process of the preceding paragraph wherein said olefinic macrolide is a dienone macrolide.

The present invention is also particularly directed to a process for preparing a microorganism capable of producing an olefinic macrolide comprising isolating from a wild-type microorganism corresponding to said microorganism a gene coding for an epoxidase activity and inactivating said epoxidase activity, wherein said gene encoding for said epoxidase activity is isolated from said wild-type microorganism via complementation.

The present invention is also directed to a process for preparing an olefinic macrolide comprising fermenting, in an aqueous nutrient medium containing assimilable sources of carbon and nitrogen, a first microorganism which has been prepared by inactivation of an epoxidase encoding gene present in the wild-type microorganism corresponding to said first microorganism.

The present invention is further directed to a process as described in the preceding paragraph which further comprises isolating said olefinic macrolide from said fermentation broth.

The present invention is particularly directed to a process as described in the preceding paragraph wherein said olefinic macrolide is a dienone macrolide.

The present invention is also directed to a process for preparing repromicin, the compound of formula (II) above, comprising fermenting a mutant microorganism, said mutant microorganism being capable of producing repromicin and incapable of producing rosamicin due to the absence of any epoxidase activity, in an aqueous nutrient medium containing assimilable sources of carbon and nitrogen to produce a fermentation broth.

The present invention is further directed to a process as described in the preceding paragraph further comprising recovering said repromicin from said fermentation broth.

The present invention is particularly directed to a process of the preceding paragraph wherein said mutant microorganism is a rosX mutant of *Micromonospora rosaria*.

The present invention is more particularly directed to a process of the preceding paragraph wherein said mutant microorganism is the rosX mutant of *Micromonospora rosaria*, said mutant which is designated as ATCC 55709.

The present invention is still further directed to a rosX mutant of *Micromonospora rosaria*.

The present invention is particularly directed to the rosX mutant of *Micromonospora rosaria* which is designated as ATCC 55709.

The present invention is also particularly directed to a rosX mutant of *Micromonospora rosaria* having all of the identifying characteristics of ATCC 55709.

The present invention is also particularly directed to a rosX mutant of *Micromonospora rosaria* which is capable of producing isolable quantities of repromicin.

The present invention is still further directed to a process for preparing repromicin, the compound of formula (11) above, comprising mutating a rosamicin-producing microorganism to produce a mutant microorganism, said mutant microorganism being capable of producing repromicin and incapable of producing rosamicin due to the absence of any epoxidase activity and subsequently fermenting said mutant microorganism in an aqueous nutrient medium containing assimilable sources of carbon and nitrogen to produce a fermentation broth.

The present invention is particularly directed to a process for preparing repromicin as described in the preceding paragraph wherein said rosamicin-producing microorganism is *Micromonospora rosaria* ATCC 29337 or *Micromonospora rosaria* ATCC 55708.

The present invention is further directed to a process as described in the preceding two paragraphs further comprising isolating repromicin from said fermentation broth.

The present invention is still further directed to a process for preparing repromicin comprising fermenting a mutant microorganism in an aqueous nutrient medium containing assimilable sources of carbon and nitrogen.

The present invention is particularly directed to a process as described in the preceding paragraph wherein said mutant microorganism is a rosX mutant of *Micromonospora rosaria*.

The present invention is still more particularly directed to a process as described in the preceding paragraph wherein said rosX mutant of *Micromonospora rosaria* is designated ATCC 55709.

The present invention is also directed to a process for preparing repromicin as described in any one of the preceding three paragraphs further comprising recovering said repromicin.

The present invention is still further directed to a process for preparing an olefinic macrolide comprising a) mutating an epoxy macrolide producing microorganism to provide a mutant microorganism, said mutant microorganism being capable of producing an olefinic macrolide corresponding to said epoxy macrolide; and b) fermenting said mutant microorganism in an aqueous nutrient medium containing assimilable sources of carbon and nitrogen.

Where used herein, the term "wild-type microorganism" refers to a microorganism having the epoxidase activity which is lacking in the corresponding mutant microorganism. Additionally, where used herein, the term "wild-type *Micromonospora rosaria*" refers to a culture of *Micromonospora rosaria* having epoxidase activity and thus being capable of producing isolable quantities of rosamicin, which epoxidase activity is lacking in the corresponding rosX mutant of *Micromonospora rosaria*.

DETAILED DESCRIPTION OF THE INVENTION

*Micromonospora rosaria* is a microorganism which produces the potent antibiotic rosamicin, which is the epoxide-containing macrolide antibiotic of formula (I) hereinabove. Within the genome of *Micromonospora rosaria* there exists an epoxidase gene which codes for an enzyme that converts the C-12/C-13 double bond of repromicin (the compound of formula 11 hereinabove) to an epoxide. As such, DNA from *Micromonospora rosaria* is used according to the process of this invention to develop a probe to determine the DNA segment which encodes for the epoxidase enzyme in other epoxy macrolide producing microorganisms.

A lyophilized sample of *Micromonospora rosaria* NRRL 3718 (ATCC 29337) has been deposited with the American Type Culture Collection, 12301 Parklawn Drive, Rockville, Md., 20852, U.S.A., under the terms of the Budapest Treaty on Sep. 05, 1995. This newly deposited culture was given the new deposit number of ATCC 55708. All restrictions on the availability to the public of the microorganism culture so deposited will be irrevocably removed upon the issuance of a patent from this application.

A rosX mutant of *Micromonospora rosaria* is a microorganism which produces the potent macrolide antibiotic repromicin, which is a derivative of rosamicin which has an olefinic bond between the C-12 and C-13 carbons rather than an epoxide. A rosX mutant of *Micromonospora rosaria* lacks the epoxidase enzyme which is present in *Micromonospora rosaria*. Therefore, the intermediate C-12/C-13 olefinic macrolide cannot be converted to the epoxy macrolide rosamicin by a rosX mutant of *Micromonospora rosaria*. As such, a rosX mutant of *Micromonospora rosaria* is used according to the process of this invention to produce repromicin via fermenting said rosX mutant and by isolating repromicin from the fermentation broth thereof according to methods well known to a person of ordinary skill in the art. This isolation may be accomplished by extracting said repromicin directly from the fermentation broth or by filtering said fermentation broth to remove the whole cells and extracting said repromicin from the filtrate. Generally the bulk of the repromicin is recovered by extracting the filtrate. However, the packed cells obtained by filtration may also be extracted to recover a small amount of repromicin. It is generally preferred to extract the repromicin from the filtrate after filtration of the fermentation broth.

A lyophilized sample of the rosX mutant *Micromonospora rosaria* (R94-304-99 SC23) has been deposited with the American Type Culture Collection, 12301 Parklawn Drive, Rockville, Md., 20852, U.S.A., under the terms of the Budapest Treaty on Sep. 05, 1995. This deposited culture was given the new deposit number of ATCC 55709. All restrictions on the availability to the public of the microorganism culture so deposited will be irrevocably removed upon the issuance of a patent from this application.

The present invention discloses the preparation of repromicin, the compound of formula (II) above. To prepare repromicin by the process of this invention, a rosX mutant of *Micromonospora rosaria*, preferably the mutant designated ATCC 55709, is inoculated into a suitable growth medium and shaken for a sufficient period of time to ensure production, such as two to four days. Shaking for three days is preferred. A preferred growth medium is JDYTT, which is prepared by mixing cerelose (10 g/L), corn starch (5 g/L) corn steep solids (2.5 g/L), NZ-amine YTT (5 g/L), $CoCl_2 \cdot 6H_2O$ (0.002 g/L), P2000 (1 mL/L) and $CaCO_3$ (3 g/L) and adding water to achieve a final volume of one liter. NZ-amine YTT is a hydrolysed protein (casein) preparation and can be purchased from Sheffield Products, Woods Corner, Norwich, N.Y. One of ordinary skill in the art will recognize that there are many other alternative products or media which will provide sufficient nutrients to ensure growth of the microorganism. Prior to use, the growth medium is adjusted to pH 7.0 using a weak anhydrous solution of hydrochloric acid if the pH is basic or a weak anhydrous solution of sodium hydroxide if the pH is acidic. When using the preferred medium, the pH of the medium is acidic and therefore must be adjusted by the addition of dilute aqueous sodium hydroxide. The growth medium is then sterilized for about 20 minutes to one hour, and preferably for 30 minutes, at elevated temperatures. A preferred temperature for sterilization is about 120° C. using the standard autoclave temperature of 121° C. Generally the mixture of microorganism and growth medium is shaken on a two inch throw shaker between 200 to 300 rpm at slightly elevated temperatures. A preferred temperature is 30° C. The term "two inch throw" refers to horizontal displacement of the flask being orbitally shaken by a shaker. One of ordinary skill in the art will recognize that any manner of providing good shaking of the mixture will suffice to mix the ingredients. About a 20% volume of a suitable cryoprotectant such as glycerol per volume of the medium is added to the microorganism growth medium mixture and the culture is stored at −80° C. for the short term (less than one year) and under liquid nitrogen for long term storage.

When needed, the frozen culture is transferred to a flask containing a sufficient amount of a suitable growth medium such as JDYTT and the culture is grown until a substantial quantity of microorganism is present. It is preferred to shake the contents of the flask at 250 rpm and at 300° C. on a two inch throw shaker for three days. However, other shaker rpms, temperatures and times may prove satisfactory to obtain effective growth of the desired microorganism.

The contents of this fermentation are added to a sufficient amount of a production medium such as RSM-6. RSM-6 is prepared by mixing corn starch (50 g/L), cerelose (10 g/L), ardamine PH (5 g/L), Pharmamedia (10 g/L), MgHPO$_4$.3H$_2$O (10 g/L), casein hydrolysate (2.5 g/L), asparagine (0.5 g/L), FeSO$_4$.7H$_2$O (0.028 g/L), MgSO$_4$.7H$_2$O (0.5 g/L), K$_2$HPO$_4$ (0.75 g/L), CuSO$_4$.5H$_2$O (0.003 g/L), P2000 (1 mL/L) and adding water to achieve a final volume of one liter. A person of ordinary skill in the art will recognize that there are other production media which may be substituted for RSM-6 with similar results. RSM-6, when used, is adjusted to pH 7.0 with a dilute aqueous solution of sodium hydroxide and is autoclaved for about 100 minutes at about 121° C. immediately prior to use. The fermentation may be carried out in any suitable fermentation vessel such as flasks, New Brunswick fermentor jars (New Brunswick, Scientific, New Brunswick, N.J.), tanks and the like. This fermentation is carried out at slightly elevated temperatures, generally about 30° C., with an agitation rate of about 100–1000 rpm. Generally, the preferred agitation rate is about 450 rpm. The agitation of the fermentation vessel provides aeration of the contents thereof. Aeration may also be accomplished by bubbling air through the mixture. Preferably, the pH of the fermentation broth is controlled during the fermentation by the addition of NaOH or H$_2$SO$_4$ as necessary so that the pH remains between 6.7 and 7.3. The fermentation will generally yield the highest titers of repromicin between about 60 and 120 hours after the fermentation is started. Samples containing repromicin are isolated from the fermentation mixture using methods well known to those skilled in the art. A suitable solvent for extracting the repromicin from the fermentation broth is any solvent or solvent mixture which will separate the repromicin from undesired by-products of the fermentation and which will not react with or otherwise adversely affect the repromicin sought to be isolated. A preferred solvent mixture for this extraction is a mixture of methanol and 0.1M potassium phosphate dihydrogen (KH$_2$PO$_4$). It is especially preferred that this mixture have a pH of 3.5 and that the relative amounts of methanol and 0.1M KH$_2$PO$_4$ are 35% methanol and 65% KH$_2$PO$_4$.

This invention is also directed to preparing a microorganism which is capable of producing an olefinic macrolide from a wild-type microorganism which ordinarily produces epoxy macrolides. The wild-type microorganisms which are used in the process of this invention are microorganisms which produce epoxy macrolides and therefore have an epoxidase enzyme which is responsible for catalyzing the intracellular reaction which converts an olefinic macrolide to the corresponding epoxy macrolide. The epoxidase enzyme which catalyzes this intracellular reaction, left unchanged, will ordinarily convert all or essentially all of the intermediate diene to epoxide. The efficiency of this intracellular process is made manifest by the inability to isolate any appreciable amounts of olefin from the fermentation broths of these microorganisms. Thus, to obtain these olefins, the microorganism must be prevented from converting the olefin to the epoxide. This is achieved by the process of this invention.

The epoxidase enzyme which is present in the wild-type *Micromonospora rosaria* ATCC 55708 is produced by *Micromonospora rosaria* using presumably ordinary cellular processes such as transcription from a DNA segment followed by translation of the RNA transcript. The DNA segment responsible for producing the epoxidase protein via this process is isolated from the DNA of the wild-type *Micromonospora rosaria* by methods well-known to those skilled in the art, such as complementation, said DNA segment being able to complement the epoxidase-deficient mutant *Micromonospora rosaria* ATCC 55709.

To obtain the DNA segment responsible for producing the epoxidase protein via complementation, the following complementation protocol is followed. The gene that directs the formation of the epoxidase responsible for epoxidating the C-12, C-13 olefin of repromicin to form the C-12, C-13 epoxide of rosamicin is cloned from the wild type *Micromonospora rosaria* by shotgun cloning and trans mutant complementation. The term "shotgun cloning" is well understood by those of ordinary skill in the art to refer to the random insertion of large numbers of different restriction fragments of DNA into bacterial plasmids. Complementation refers here to the ability of a cloned genomic fragment to direct the synthesis of the epoxidase and to produce wild type phenotype when introduced in trans configuration in *Micromonospora rosaria* rosX cells. Trans configuration refers to the intracellular presence of two epoxidase genes on two different molecules of DNA. In a trans complementation analysis, the mutated epoxidase gene forms part of the genome or chromosome of the host culture, and the normal or wild type epoxidase gene is located on a vector or plasmid molecule. Though trans complementation is preferred, one of ordinary skill in the art would recognize that cis complementation may also be used in this complementation protocol.

The *Micromonospora rosaria* rosX cells are unable to produce rosamicin because the microorganism lacks the epoxidase enzyme responsible for epoxidating the C-12, C-13 olefin of repromicin. As a consequence, the latter compound accumulates in the mutated culture. However, when a particular DNA fragment having the ability to direct the synthesis of the epoxidase enzyme is introduced into the *Micromonospora rosaria* rosX cells by standard transformation procedures, the component missing or rendered inactive by the mutation (the epoxidase enzymatic function) is restored. Therefore, as a result of the complementation experiment, the mutated culture recovers the ability to epoxidate repromicin to form rosamicin and now exhibits a wild type phenotype. This complementation test is used to identify and clone the DNA fragment carrying the epoxidase gene from a *Micromonospora rosaria* genomic library.

The first step to clone the gene that governs the formation of the epoxidase protein from *Micromonospora rosaria* is to construct a genomic library. This library consists of DNA chromosomal fragments prepared from the wild type *Micromonospora rosaria* (e.g., the strain ATCC 55708 described in this application). The terms genomic and chromosomal libraries are used here as synonyms and refer to a set of cloned DNA fragments together representing the entire genome of the wild type *Micromonospora rosaria*. It is well known to one of ordinary skill in the art that *Micromonospora rosaria* is a gram-positive organism having an extremely high G+C content (about 70%) within its chromosomal DNA. Like other Actinomycetes species, *Micromonospora rosaria* is expected to have a relatively large genome. This genome complexity makes the cloning of large fragments particularly useful when constructing a *Micromonospora rosaria* DNA library. Assuming random DNA cleavage and optimal representation of the chromosome in the clone library, the number of clones to be screened is related both directly to genome size and inversely to the average size of the DNA inserts. Therefore, to reduce the number of clones to be screened for the epoxidase gene it is advantageous to clone large pieces of DNA. Further, this is extremely helpful in minimizing the number of analyses and manipulations required to establish a restriction map of a large chromosomal region by identifying contiguous or overlapping clones. Techniques for preparing genomic libraries are well known to those of ordinary skill in the art. A general description of the preparation of genomic libraries is disclosed in Sambrook, J., E. F. Fritsch, and T. Maniatis, "Molecular Cloning: A Laboratory Manual", 1989, 2nd ed., Cold Spring Harbor Laboratorcomplete description of bor, N.Y. A complete description of actinomycetes chromosomal library preparation is disclosed in Hopwood, et al., "Genetic manipulation of Streptomyces—A Laboratory Manual", 1985, The John Innes Foundation, Norwich, UK.

The chromosomal DNA is prepared from a culture of *Micromonospora rosaria* ATCC 55708 grown in liquid medium as described above. Mycelium is recovered by centrifugation and genomic DNA is prepared following the protocol found in Hopwood, et al. supra. DNA pellets are usually resuspended in an aqueous buffer such as TE buffer (10 mM Tris-HCl, pH 8.0; 1 mM EDTA). The chromosomal DNA is then partially digested with a restriction enzyme such as HaeIII or Sau3A. Sau3A is preferred because it recognizes 4-base sequences which produce a random collection of insert fragments. Enzymes which recognize 6-base sequences may also be used in this procedure but are less preferred since such enzymes recognize a less random collection of insert fragments than do enzymes which recognize 4-base sequences. The fragments are ligated into the unique BamHI site present in the multiple cloning site of a vector. The preferred vector is pCD425, a cosmid shuttle vector, although it will be understood by one of ordinary skill in the art that other shuttle vectors can be used. A full description of pCD425 and other shuttle vectors useful for cloning in actinomycetes can be found in European Patent Publication Number 0 620280.

It is advantageous to clone the genomic fragments in a vector that can transform both *Escherichia coli* and *Micromonospora rosaria*. Cosmid shuttle vector pCD425 exhibits a high copy number in *Escherichia coli* cells and a low copy number in actinomycetes cells. Further, it is preferred that a vector exhibiting a low or single copy number per genome in *Micromonospora rosaria* is used. pCD425 is a preferred low copy number vector which has the ability to stably maintain large DNA fragments (up to 40 kb) and to avoid possible gene dosage effects. The person of ordinary skill in the art would recognize that there are alternative low copy number vectors which are useful in this invention, such as pCD396, which is disclosed in European Patent Publication Number 0 618297. Both pCD396 and pCD425 have the widely used ColE1 origin of replication (see Sambrook, J. et al., infra) which allows replication in all *Escherichia coli* strains commonly used in recombinant DNA experiments, and the SCP2* origin of replication that allows the maintenance of a low copy number and a broad host range in actinomycetes (see Lydiate, D. J., Malpartida, F., and Hopwood, D. A., Gene, 35, 223–235, 1985). These vectors also carry the tsr gene, which confers resistance to the antibiotic thiostrepton upon transformation into actinomycetes cells, and the amp gene, which confers resistance to the antibiotic ampicillin upon transformation into *Escherichia coli* cells. The tsr gene and the amp gene are used to select the transformed cells from the cell mixture. Further, shuttle vector pCD425 is a cosmid vector that has AT-rich recognition sequences for several restriction enzymes flanking the BamHI cloning site. Since AT-rich recognition sequences are infrequently represented in the *Micromonospora rosaria* genome, there is a great chance to find at least one of these enzymes which will allow the recovery of the epoxidase gene-containing, GC-rich genomic DNA insert as a single restriction fragment. This feature is useful for the in vitro reconstruction and mapping of a large chromosomal region containing the epoxidase gene in *Micromonospora rosaria*. A description of cosmid vectors in general and a list of alternative cosmid vectors is disclosed in Sambrook, et al., supra. In this manner the entire genome of the wild type *Micromonospora rosaria* culture can be represented in the form of randomly generated DNA fragments which are ligated to shuttle vector pCD425. The genomic library constructed as described above can then be used for a shotgun experiment. Shotgun experiment refers to the identification and cloning of a particular DNA fragment carrying the epoxidase gene from a library of randomly generated DNA fragments ligated to a vector.

Plasmid DNA can be prepared from the *Micromonospora rosaria* genomic library constructed in *Escherichia coli* by a modification of the method of Birnboim and Doly described in Birnboim et al., Nucleic Acids Research, 1979, 7, 1513–1525. Other procedures for preparing plasmid DNA are found in Sambrook, supra. The plasmid DNA preparation is then used to transform directly *Micromonospora rosaria* rosX protoplasted cells. Protoplasts of the *Micromonospora rosaria* rosX cells are prepared following standard procedures as those described by Hopwood et al., supra.

Alternatively, plasmid DNA prepared from the *Micromonospora rosaria* genomic library constructed in *Escherichia coli* is used to transform an intermediate host cell such as *Streptomyces lividans* TK64 cells. Thus, a genomic library of *Micromonospora rosadia* DNA is obtained in an intermediate host such as *Streptomyces lividans*. Plasmid DNA is prepared from the host library and this plasmid DNA is used to transform *Micromonospora rosaria* protoplasts by following protocols similar to those described hereinabove. This procedure results in a higher efficiency of transformation of *Micromonospora rosaria* cells than can be achieved when using plasmid DNA prepared from *Escherichia coli* cells directly. Protocols used for the preparation of *Streptomyces lividans* protoplasts, *Streptomyces lividans* transformation, and preparation of plasmid DNA from *Streptomyces lividans* hosts are well known to those skilled in the art and are found in Hopwood, et al., supra and in International Patent Application Publication Number WO95/16781.

Upon transformation of *Micromonospora rosaria*, cell transformants able to grow on agar plates containing the antibiotic thiostrepton (thiostrepton resistant (tsr-R) transformants) are first selected from agar plates containing the antibiotic thiostrepton as a selective factor. These transformants are detected by visual observation of the agar plates. Those transformants which are thiostrepton resistant are then screened for rosamicin production. Thus, the fermentation products made by the transformants are recovered in the usual manner such as by extraction. These transformants are grown in a suitable liquid media such as RSM-6, described hereinabove, and the rosamicin is extracted therefrom according to usual methods of macrolide isolation as described herein. The macrolide obtained is characterized by HPLC. A culture exhibiting a Rosamicin+ phenotype is assumed to be due to complementation of the rosX mutation. Representative Rosamicin+ transformants are then grown under nonselective conditions (following protoplast formation and regeneration), which allows for plasmid loss, and resulting thiostrepton sensitive (tsr-S) colonies are isolated and tested for antibiotic production. These colonies have lost the ability to produce detectable amounts of rosamicin, and produced repromicin instead. The latter is a strong indication that the Rosamicin+phenotype was due to the presence of the transforming DNA and not due to reversion of the rosX mutation.

Plasmid DNA from the transformed *Micromonospora rosaria* cultures is then rescued by transforming *Escherichia coli* DH5-alpha competent cells with total DNA recovered from representative Rosamicin+ transformants. Competent *Escherichia coli* cells such as *Escherichia coli* strain DH5-alpha cells (purchased from life Technologies, Inc., Gaithersburg, Md.) are transformed with purified plasmid DNA by the method recommended by the suppliers. Recovered ampicillin-resistant transformants are grown, plasmid isolated and analyzed following standard procedures as described in Sambrook, et al., supra and elsewhere as is known to those skilled in the art. In addition, plasmid DNA is also prepared from the original *Escherichia coli* library clone. A restriction analysis performed by comparison of the agarose gel electrophoretic profiles of the original library plasmid and reisolated plasmids should be indistinguishable in all cases. This analysis shows if the plasmids existed as the unaltered free replicons in the Rosamicin+ transformants.

The epoxidase activity is then mapped in the cloned DNA fragment by a combination of deletional analysis and subcloning followed by complementation. To determine which region of the cloned DNA fragment encodes the epoxidase, a series of DNA segments from this region is subcloned into shuttle vector pCD425 using similar procedures to those described above. These new constructs are then transformed in *Micromonospora rosaria* rosX ATCC 55709 cells and the new transformants are screened for repromicin production. A subclone is identified by its ability to restore production of rosamicin in the rosX mutant culture. The smallest cloned DNA fragment exhibiting the ability to complement the rosX mutation is sequenced. A preferred sequencing method is the dideoxy sequencing method described in Sanger, et al.,  Proc. Natl. Acad. Sci. USA, 1977, 74, 5463–5467. The sequence is then analyzed for the epoxidase coding region, using a sequence analysis program. Preferred software for performing this sequence analysis is CodonPreference+, which is a trademark of the Genetics Computer Group, Inc., Madison, Wis. This software can be obtained from the Genetics Computer Group, Inc., Madison, Wis. When performing this sequence analysis, a person of ordinary skill in the art looks for the characteristic codon usage and G+C third-position bias of actinomycetes genes. Using this procedure the open reading frame containing the entire epoxidase gene is identified.

The term "open reading frame", where used herein, refers to a continuous sequence of genetic information without any termination signal. The sequence is translatable into a protein. In particular in this invention, the open reading frame contains the sequence information needed to direct the synthesis of the epoxidase enzyme during the process of translation.

To those skilled in the art it is known that alternative approaches to the complementation procedure described above can be employed to clone the gene that encodes the epoxidase protein responsible for epoxidating the C-12, C-13 olefin of repromicin to form the C-12, C-13 epoxide of rosamicin from the wild type *Micromonospora rosaria*. In particular, two alternative approaches include reverse genetics and homology probing. In reverse genetics, the epoxidase enzyme is purified using standard procedures of protein purification and the N-terminal amino acid sequence of the epoxidase enzyme is determined. Then, based upon this amino acid sequence, a DNA sequence is deduced and used to prepare a synthetic DNA probe. This probe is then used to clone the epoxidase gene from the wild type *Micromonospora rosaria* genomic library by using a conventional hybridization-based screening approach. Homology probing is accomplished by deducing synthetic DNA primers or synthetic oligomeric DNA probes by comparing other related epoxidases available from the literature. These DNA primers or synthetic oligomeric DNA probes are then used to clone the gene from the wild type *Micromonospora rosaria* genomic DNA using either PCR or hybridization techniques or a combination of both. These and other approaches are well known to those skilled in the art and a general description of these methods can be found in Sambrook, et al, supra.

A fragment of this DNA segment is used as a probe to determine the DNA segment responsible for producing the epoxidase enzyme which catalyzes the intracellular epoxidation of olefins in other wild-type microorganisms which generally produce epoxy macrolides. It is well-known to those of ordinary skill in the art how a small DNA segment from one microorganism can be used as a probe for segments having similar sequences in other microorganisms. This procedure is described, for example, in many standard laboratory manuals, such as *Current Protocols in Molecular Biology*, Greene Publishing Associates and Wiley-Interscience, John Wiley & Sons, NY (1987). Using these techniques, the DNA segment coding for the epoxidase enzyme which is responsible for catalyzing the intracellular epoxidation of olefinic macrolides to epoxy macrolides found in microorganisms capable of producing epoxy macrolide antibiotics can readily be determined. The following table contains a list of microorganisms which are capable of producing an epoxy macrolide antibiotic and the epoxy macrolide antibiotic which is produced by the microorganism. This table is exemplary in nature and is not intended to include all of the microorganisms capable of producing epoxy macrolide antibiotics. One of ordinary skill in the art will readily appreciate that the process of this invention of preparing a microorganism capable of producing an olefinic macrolide is capable of being carried out with any microorganism capable of producing epoxy macrolides, including but not limited to the microorganisms listed in Table I below.

TABLE 1

16-Membered Ring Macrolides Containing Epoxy Groups.
Source: S. Omura and H. Tanaka, *Macrolide Antibiotics*, S. Omuara, Ed., 1984, Academic Press, Orlando, FL 32887, pp.3–36, ("Production and Antimicrobial Activity of Macrolides").

| Macrolide(s) | Microorganism |
| --- | --- |
| Maridomycins I, II, III, IV, V and VI | *S. hygroscopicus* |
| Carbomycin A | *S. halstedii* |
| Cirramycin A₁ | *S. cirratus* |
| Angolamycin | *S. eurythemus* |
| 20-Dihydroangolamicin | Streptomyces sp. SK-62 |
| Mycinamicins I and II | *M. griseorubida* |
| Chalcomycin | *S. albogriseolus* |
| Neutramycin | *S. rimosus* |
| Deltamycins A1, A2 and A3 | *S. deltae* |
| B-5050 G | *S. hygroscopicus* |
| Staphcoccomycin | Streptomyces sp. AS-NG-16 |

A segment of DNA encoding for the epoxidase enzyme is found, using procedures well-known to those of ordinary skill in the art, from a strain of a microorganism which produces an epoxy-dienone macrolide. To accomplish this, total genomic DNA is hybridized with the probe DNA segment, which has already been isolated from *Micromonospora rosaria*. The hybridization is accomplished using methods well-known to those of ordinary skill in the art. Thus, generally the genomic DNA is cut into DNA fragments using restriction enzymes, such as Bam H1, EcoR1 or other well-known restriction enzymes. It is preferred that the fragments which result are in the range of about 1 kb to about 10 kb. Of course there will generally be fragments which are smaller or larger than 1–10 kb depending upon the sequence of the particular DNA and the particular restriction enzymes chosen. These fragments are analyzed using electrophoresis, generally using an agarose gel. After separation has been achieved, the fragments are transferred to a nitrocellulose filter and the DNA is melted to separate the strands using a suitable temperature such as 90° C. to 100° C. The probe from *Micromonospora rosaria* is made radioactive using well-known techniques and is added to the filter in an aqueous solution. The temperature is lowered to about 45° to 65° C. to re-anneal the DNA. One of ordinary skill in the art will recognize that the optimum for re-annealing is dependent upon the specific DNA sequence of the particular microorganism being hybridized. The probe will bind to only that DNA strand which has a substantially complementary nucleotide sequence. The degree of complementarity which will be necessary for the probe to hybridize with the DNA is controlled by the temperature of the hybridization reaction.

After obtaining the hybrid DNA, the filter is washed and dried and the probe/DNA segment hybrid is detected by the use of X-ray film autoradiography. If a DNA fragment is hybridized as determined by X-ray film autoradiography, then a DNA library is prepared from the strain of interest using methods well-known to those of ordinary skill in the art. This library is itself then probed with the original radioactive probe from *Micromonospora rosaria* to determine which colony in the library contains the gene of interest.

The DNA from the colony of interest is then cleaved using various restriction enzymes until a DNA fragment which is small enough to sequence conveniently is obtained. Those of ordinary skill in the art will appreciate that this often requires the preparation of a restriction map which organizes the results of the cleavages. When a sufficiently small DNA fragment which contains the gene of interest which hybridizes with the probe is obtained, the fragment is sequenced using procedures well-known to those of ordinary skill in the art to determine the nucleotide sequence thereof. Generally it is preferred that the DNA fragment contain only one gene with a few extraneous nucleotide bases attached to either end. However, occasionally it will be impractical to reduce the size of the DNA fragment to be sequenced to less than about 2–5 kb. In those instances, the larger DNA fragment is sequenced. The DNA sequence of the gene which expresses the protein which catalyzes epoxidation is thus obtained by this method.

To deactivate this DNA sequence so that it is incapable of expressing the epoxidase enzyme for the microorganism of interest, a portion of the DNA of the gene is excised. Generally the amount of DNA which is removed is about 1 to 30 nucleotide bases in size, although more bases may be removed depending upon the particular gene which is being deactivated and the method used to deactivate the gene. The excision of nucleotide bases from the gene is accomplished using methods well-known to those of ordinary skill in the art, such as but not limited to the use of restriction enzymes either alone or in combination with exonucleases, and the use of the polymerase chain reaction (PCR) in combination with a pair of specific mutagenic primers specifically targeting the epoxidase-encoding gene. After the excision has been accomplished, if the nucleotide bases have been removed from an interior portion of the gene, then the two DNA fragments thus generated will be ligated to form a gene containing a deletion. This engineered, defective gene is then sequenced to determine the nucleotide sequence of the defective gene. One of ordinary skill in the art will recognize that a deletion will ordinarily result in the deactivation of the gene's ability to express an active protein. However, rarely, a deletion may not result in such a deactivation. In those rare circumstances, a different portion of the nucleotide sequence will be required to be deleted to deactivate the gene.

Alternatively, to assure a complete inactivation of the epoxidase gene an antibiotic marker is inserted in place of the deleted sequence. The preferred antibiotic marker for this work is the ermE gene of *Saccharopolyspora erythraea* (formerly *Streptomyces erythraeus*). For a description of this marker, see Hopwood, et al., supra. This marker confers resistance to erythromycin to the transformed *Micromonospora rosaria* cells. Additional useful markers conferring resistance to other antibiotics such as neomycin, hygromycin, viomycin can be used with a similar purpose. For a list of these markers, including complete restriction map information, see D. A. Hopwood et al., supra. Standard cloning procedures are used to insert the ermE marker in the deletion site of the epoxidase gene. The marker is positioned in an orientation opposite to that of the epoxidase open reading frame, to avoid a possible lethality caused by overexpression of downstream genes. To insert this marker to disrupt a gene of interest see International Patent Publication Number WO95/16781. The antibiotic marker inserted in the truncated epoxidase gene will facilitate the replacement of the mutated gene in the wild type strain allowing to monitor the success of the gene replacement experiment in the microorganism of interest as it will be discussed in the following sections.

The wild-type microorganism of the strain from which the gene that was deactivated was obtained, which is capable of epoxidating the diene to form an epoxide, is then manipulated to contain the engineered, deactivated gene. This is accomplished according to gene replacement methods well-known to those of ordinary skill in the art. Generally, the gene is inserted into a DNA delivery vector such as a bacteriophage, plasmid or cosmid. It is preferred to use a plasmid to deliver the engineered gene to microorganisms useful in the present invention by techniques well-known to those of ordinary skill in the art such as transformation or conjugation. Transformation is accomplished by transforming the microorganism with the plasmid, which transfers the engineered gene to the DNA of the microorganism.

The transfer of the mutated gene into the chromosome of the microorganism of interest occurs by recombination between the host chromosome and the plasmid containing a homologous region to it. It is assumed that the replacement of the genomic segments with altered DNA sequences on the plasmid depends on in vivo homologous recombination. Presumably, two crossovers occurring simultaneously, or a single crossover leading to integration and a subsequent resolution step where the integrated plasmid is excised, cause reciprocal exchange between the cloned and resident sequences. By using this approach it is possible to disrupt the open reading frame of the gene encoding the epoxidase enzyme. The disruption involves either a chromosomal deletion or an insertion of an antibiotic marker or both. The resulting mutant strain, which lacks the epoxidase activity, is stable and can be used to generate valuable olefinic macrolides which are isolable by fermentation.

The construction of the plasmid, also named integration vector, constitutes a crucial step in the development of the mutated strain by gene replacement. One important characteristic of the integration vector is that after replacing the genes in the actinomycetes chromosome, the vector is completely eliminated from the host cells. A number of vectors are disclosed in Kieser, T., and Hopwood, D. A., Methods in Enzymology, 1991, vol. 204, 430–458). In the instant invention, shuttle vector pCD262 is employed in the construction of an epoxidase-deficient strain of the microorganism of interest. This vector forms part of a set of versatile shuttle vectors useful for cloning both in actinomycetes and in *Escherichia coli*, and for a variety of gene replacement applications in actinomycetes. See, for example, European Patent Application Publication Number 0 618297. Vector pCD262 carries an origin of replication that controls for a moderate-to-high copy number in actinomycetes. When *Micromonospora rosaria* cells that have been transformed with the vector are submitted to stress, such as high temperature, sporulation, or protoplasting and subsequent regeneration, numerous plasmid-free colonies can be recovered.

The construction of the plasmid carrying an inactivated version of the gene encoding the epoxidase protein involves the cloning of the deactivated epoxidase gene into the integration vector. The deactivated epoxidase gene is located approximately in the middle of the *Micromonospora rosaria* genomic fragment. This fragment should be at least 3 kb long to facilitate the exchange of the epoxidase genes (deactivated and wild type) at high frequency. It is understood by the person of ordinary skill in the art that the fragment is limited in size by the particular shuttle vector being used. The integration vector contains several marker genes such as amp, which confers resistance to ampicillin when the vector is replicating in *Escherichia coli* cells, and tsr, which confers resistance to thiostrepton when the vector is introduced by transformation in *Micromonospora rosaria* cells. In addition, the integration vector contains the ermE marker inserted in the middle of the inactivated epoxidase gene, which confers resistance to erythromycin in the *Micromonospora rosaria* transformed cells. The preferred vector for these manipulations is shuttle vector pCD262. However, it will be understood by those of ordinary skill in the art that other integrating vectors and antibiotic markers can also be used effectively to construct the plasmid (see Kieser, T., and Hopwood, D. A., 1991, Genetic Manipulation of Streptomyces: Integrating Vectors and Gene Replacement, in: Methods in Enzymology, vol. 204, 430–458). Upon transformation, the colonies which have been transformed are challenged with an antibiotic which kills all microorganisms which do not contain the marker gene used to inactivate the epoxidase open reading frame. The only cells which remain are those which have taken up the integration vector. Among these will be those cells that have the defective engineered gene inserted in the chromosome and no wild-type epoxidase expressing gene. The transformed microorganism containing the defective engineered gene is then fermented using methods of fermentation well-known to those of ordinary skill in the art. Since the microorganism is already known to produce an epoxide containing macrolide, a standard fermentation procedure will already have been established for this microorganism. The fermentation broth is analyzed for the presence of the epoxidated macrolide which is formed by the wild-type microorganism. The absence of epoxidated macrolide which the wild-type microorganism originally produced and the presence of the diene macrolide indicate that the microorganism has been successfully engineered to produce only the diene macrolide precursor. The diene macrolide is isolated using methods well-known to those of ordinary skill in the art.

To convert the wild-type microorganism into a microorganism which is incapable of producing an epoxy macrolide and which therefore produces an olefinic macrolide as its final and isolable product, the gene present in the wild-type microorganism can also be inactivated by chemical mutagenesis at the molecular level or by other methods well-known to those skilled in the art such as gene disruption. It will be recognized by one of ordinary skill in the art that any methodology involving molecular genetics applications will require identification of the gene as described hereinabove. The inactivated gene is then incapable of synthesizing the epoxidase enzyme in the microorganism. The antibiotic synthesis undertaken by the microorganism thus stops at the olefin stage. The olefin is isolated using the procedures taught herein for isolating repromicin or other standard procedures well-known to those skilled in the art.

To obtain a rosX mutant of *Micromonospora rosaria* ATCC 55709, a culture of the wild-type *Micromonospora rosaria* is mixed with a suitable growth medium and is shaken at 200–225 rpm at 28° C.–30° C. It will be understood by those skilled in the art that this mutagenesis procedure can be carried out on any culture or mutant of *Micromonospora rosaria* which contains epoxidase activity to prepare a rosX mutant of *Micromonospora rosaria*. Suitable growth media are well known to those of ordinary skill in the art. A preferred growth media for the growth of *Micromonospora rosaria* is YPD-6 medium. It is generally preferred to use one half strength YPD-6 medium. It is preferred that the culture of *Micromonospora rosaria* be a lightly grown culture. A lightly grown culture is a culture with a slight visible turbidity as compared to a fully grown culture which exhibits dense, heavy growth. One-half strength YPD-6 is prepared by mixing Difco Yeast Extract (5 g/L), Bacto peptone (5 g/L), dextrose (2.5 g/L) MOPS buffer (5 g/L) and adding enough water to bring the final volume to one liter. The pH is adjusted to pH 7.0 with dilute aqueous sodium hydroxide. This culture is treated with a suitable chemical mutagenesis inducing agent such as methanesulfonic acid, ethyl ester (EMS) or sodium bisulfite. Concentrations of the mutagenic agent can be determined empirically using the criteria set forth hereinbelow. When EMS is used, for example, the amount of EMS is generally about 15–40 µL for a lightly grown 2 mL aliquot of a culture of the microorganism. The preferred mutagenesis inducing agent is EMS. The mutagenesis reaction is incubated at temperatures such as 15° C. to 40° C. for 3 to 10 hours. It is preferred that the mutagenesis reaction be carried out at 30° C. for 4.5 to 5 hours with shaking. It is also preferred that the mutagenesis reaction flask be shaken at 30° C. at 200–225 rpm. The mutagenesis reaction culture is diluted with a suitable medium such as fresh SCM medium and is centrifuged. The supernatant is generally removed and discarded. The cell pellets from the centrifugation are resuspended in fresh growth medium. It is generally preferred that this growth medium be identical to the growth medium which is used during the initial growth of the wild-type *Micromonospora rosaria*. This is titered on solid medium to determine the number of mutagenesis survivors. The protocol is continued only if one thousand or more colonies remain. If fewer colonies are found, the above procedure is generally repeated and less EMS (15–20 µL) is used. If less than 50% killing of the colonies is observed, compared to a non-mutagenized control, then the above procedure may be repeated and more EMS (30 to 50 µL) will be used. The tubes containing survivors are incubated for 2–3 days until the culture is fully grown. Sterile glycerol (80%, 2 mL) is added to each survivor tube and each tube is placed in a freezer at −20° C. After 24–48 hours, the frozen culture is titered for future reference. To isolate the rosX mutant, single colonies of the frozen stock of mutagenized parental culture are grown up and are fermented in 2 mL cultures. The products of this culture are examined after the broths are extracted with 8 mL of extraction buffer and are run through an HPLC. The extraction buffer which is used to extract the mutant is identical to the "mobile phase" which is used in the HPLC analysis. One of ordinary skill in the art will recognize that there are other mutagenesis procedures which are capable of producing the rosX mutant of *Micromonospora rosaria*.

The utility of the macrolide olefins which are prepared by the process of this invention as antibiotics is demonstrated by testing said compounds using procedures well known to those of ordinary skill in the art such as those disclosed in Wagman et al., Journal of Antibiotics, 1972, 25, 641–646.

Where used herein, the term "HPLC" refers to "high performance liquid chromatography," which is an analytic and isolation technique used by those of ordinary skill in the art.

The present invention is illustrated by the following examples, but is not limited to the details thereof. P-2000 is polypropylene glycol and is purchased from George Mann & Co., Inc., 175 Terminal Road, Providence, R.I., 02905. Pharmamedia is a cottonseed-derived protein nutrient and is purchased from Traders Protein, The Buckeye Cellulose Corporation, P.O. Box 8407, Memphis, Tenn., 38108. Ardamine PH is purchased from Champlain Industries Inc., 79 State Street, Harbor Beach Mich., 48441. Pepticase is purchased from Sheffield Chemical, Norwich, N.Y.

EXAMPLES

Example One

1. Preparation of Repromicin—Fermentor scale

To prepare frozen lots for use as standard inoculum, *Micromonospora rosaria* was inoculated into JDYTT medium (cerelose 10 g/L, corn starch 5 g/L, corn steep solids 2.5 g/L, NZ Amine YTT 5 g/L, $CoCl_2.6H_2O$ 0.002 g/L, P2000 1 ml/L, $CaCO_3$ 3 g/L) and shaken (250 rpm, 300° C., 2 inch throw) for about three days. The JDYTT medium, adjusted to about pH 7.0, was sterilized at about 121° C. for about 30 minutes prior to use. After cell growth was completed, glycerol (final concentration 20%) was added as a cryoprotectant, and the culture was stored at about −80° C.

To prepare the inoculum, 5 ml of the frozen culture lot was transferred to 1 liter of JDYTT medium in a 2.8 L fernbach flask. The culture was grown for about 3 days at about 30° C. with shaking (250 rpm, 2 inch throw). The entire contents of the fernbach were transferred to 8 L of production medium RSM-6 in a 14 L fermentor jar (New Brunswick Scientific, New Brunswick, N.J.) with two 4¾ inch agitator blades. The composition of RSM-6 was corn starch 50 g/L, cerelose 10 g/L, ardamine PH 5 g/L, Pharmamedia 10 g/L, $MgHPO_4.3H_2O$ 10 g/L, casein hydrolysate 2.5 g/L, asparagine 0.5 g/L, $FeSO_4.7H_2O$ 0.028 g/L, $MgSO_4.7H_2O$ 0.5 g/L, $K_2HPO_4$ 0.75 g/L, $CuSO_4.5H_2O$ 0.003 g/L, $MnCl_2.4H_2O$ 0.003 g/L, $ZnSO_4.7H_2O$ 0.003 g/L, $CoCl_2.6H_2O$ 0.003 g/L, P2000 1 ml/L RSM-6 was adjusted to about pH 7.0 with dilute, aqueous NaOH and autoclaved for about 99 minutes at about 121° C. prior to use. The fermentations were run at about 30° C., 450 rpm, 0.34 v/v/m air, with pH controlled between 6.7 and 7.3 with NaOH/ $H_2SO_4$ or by addition of 6 g/L MOPS to production medium. Repromicin titers typically peaked between 69 and 116 hours. Samples were extracted into a solvent mixture (3.5:6.5 methanol:0.1M $KH_2PO_4$ buffer, pH 3.5) for assay by HPLC (Inertsil C-8 column,Su, 250×4.6 mm (Metachem Technologies, Torrance, Calif.), 30° C., flow rate of 0.6 ml/min., detected via UV at 280 nm, mobile phase $H_2O$:acetonitrile:THF::60:28:12, 0.05% trifluoroacetic acid). *Micromonospora rosaria* R94-304-99 SC23 (ATCC 55709) produced 368–398 mg/L repromicin under these conditions.

2. Preparation of Repromicin—Flask scale

Inoculum was prepared as described above or by adding 2 ml of frozen culture lot to 30 ml JDYTT inoculum medium in a 300 ml Erlenmeyer flask. The culture was grown for about 3 days at about 30° C. with shaking (250 rpm, 2 inch throw). Two ml of inoculum were transferred into about 30 ml modified RSM-5 medium (corn starch 30 g/L, 10 g/L Pharmamedia, 10 g/L cerelose, 5.0 g/L ardamine PH, 0.5 g/L asparagine, $FeSO_4.7H_2O$ 0.028 g/L, $MgSO_4.7H_2O$ 0.5 g/L, $K_2HPO_4$ 0.75 g/L, $CuSO_4.5H_2O$ 0.002 g/L, $MnCl_2.4H_2O$ 0.003 g/L, $ZnSO_4.7H_2O$ 0.003 g/L, MOPS 6 g/L, casein hydrolysate 2.5 g/L and $MgHPO4.0.3H_2O$ 10 g/L, P2000 1 ml/L, pH 7.0 (adjusted with dilute, aqueous NaOH), autoclaved at about 121° C. for about 20 minutes) in a 300 ml Erlenmeyer flask. Flask runs were shaken for 3–4 days at about 30° C. Fermentation broth was extracted as described above and submitted for HPLC assay. *Micromonospora rosaria* R94-304-99 SC23 (ATCC 55709) produced 455 mg/L repromicin under these conditions.

Example Two

Preparation of the rosX mutant of *Micromonospora rosaria*

A fresh, lightly grown culture of *Micromonospora rosaria* (10 mL) was mixed with one-half strength YPD-6 medium and was shaken at 200–225 rpm at 28° C.–30° C. A lightly grown culture is a culture with a slight visible turbidity as compared to a fully grown culture which exhibits dense, heavy growth. One-half strength YPD-6 was prepared by mixing Difco Yeast Extract (5 g/L), Bacto peptone (5 g/L), dextrose (2.5 g/L) MOPS buffer (5 g/L) in enough water so that the total volume of the mixture was one liter. The pH was adjusted to pH 7.0 with dilute aqueous sodium hydroxide.

Methanesulfonic acid, ethyl ester (EMS, 25 μL) was added to this culture/medium mixture (2 mL) and the reaction mixture was incubated at 30° C. for 4.5 to 5 hours with shaking at 200–225 rpm. The culture was diluted with fresh SCM medium (8 mL). This was centrifuged and the supernatant was carefully removed and discarded.

The cell pellets from the centrifugation were resuspended in fresh one-half strength YPD medium (2 mL) and were titered on solid medium to determine the number of mutagenesis survivors. The protocol was continued only if one thousand or more colonies remained. If fewer colonies were found, the above procedure was repeated and less EMS (15–20 μL) was used. If less than 50% killing of the colonies was observed, compared to a non-mutagenized control, then the above procedure was repeated and more EMS (30 to 50 μL) was used. In this experiment, 25 μL yielded colonies within the desired range so that the procedure could be continued.

The tubes containing survivors were incubated for 2–3 days until the culture was fully grown. Sterile glycerol (80%, 2 mL) was added to each survivor tube and each tube was placed in a freezer at −20° C. After 24–48 hours, the frozen culture was titered for future reference.

To isolate the rosX mutant, single colonies isolated on YPD agar medium from the frozen stock of mutagenized parental culture were grown up and were fermented in 2 mL cultures. The products of the cultures were examined after the broths were extracted with 8 mL of extraction buffer and were analyzed by HPLC. The extraction buffer which is used to extract the mutant is identical to the "mobile phase" which is used in the HPLC analysis. Samples were extracted into a solvent mixture (3.5:6.5 methanol:0.1M $KH_2PO_4$ buffer, pH 3.5) for assay by HPLC (Inertsil C-8 column,Su, 250× 4.6 mm (Metachem Technologies, Torrance, Calif.), 30° C., flow rate of 0.6 ml/min., detected via UV at 280 nm, mobile phase $H_2O$:acetonitrile:THF::60:28:12, 0.05% trifluoroacetic acid). Repromicin has a $UV_{max}$ of 288 and typically takes 50% more time to elute than rosamicin. Thus, repromicin can be differentiated from rosamicin by co-running a sample of the product of this example and repromicin together. The $UV_{max}$ for rosamicin is 242 nm. The rosX mutant of *Micromonospora rosaria* was detected and isolated on the basis of its production of repromicin and the absence of any rosamicin.

We claim:

1. A process for preparing a microorganism that produces an olefinic macrolide comprising inactivating epoxidase activity of a wild-type epoxy macrolide producing microorganism.

2. The process of claim 1 wherein said olefinic macrolide is a dienone macrolide.

3. The process of claim 2 further comprising isolating a gene coding for said epoxidase activity from said wild-type epoxy macrolide producing microorganism and inactivating said gene.

4. The process of claim 3 wherein said olefinic macrolide is a dienone macrolide.

5. The process of claim 3 wherein said gene coding for said epoxidase activity is isolated from said wild-type epoxy macrolide producing microorganism via complementation.

6. A process for preparing an olefinic macrolide comprising a) fermenting a microorganism prepared according to the process of claim 3 in an aqueous nutrient medium containing assimilable sources of carbon and nitrogen to produce a fermentation broth; and b) isolating said olefinic macrolide from said fermentation broth.

7. The process of claim 6 wherein said olefinic macrolide is a dienone macrolide.

8. A process for preparing repromicin comprising a) fermenting a mutant microorganism obtained according to the process of claim 3 in an aqueous nutrient medium containing assimilable sources of carbon and nitrogen to produce a fermentation broth; and b) recovering said repromicin from said fermentation broth.

9. The process of claim 8 wherein said mutant microorganism is a rosX mutant of *Micromonospora rosaria*.

10. The process of claim 9 wherein said rosX mutant of *Micromonospora rosaria* is designated ATCC 55709.

11. The process of claim 9 wherein said mutant microorganism is the rosX mutant of *Micromonospora rosaria*, said mutant also designated as ATCC 55709.

12. A rosX mutant of *Micromonospora rosaria*.

13. The rosX mutant of claim 12 which is designated ATCC 55709.

14. The rosX mutant of claim 12 having all of the identifying characteristics of ATCC 55709.

15. The rosX mutant of *Micromonospora rosaria* of claim 12 which produces repromicin.

16. A process for preparing repromicin comprising a) mutating a rosamicin-producing microorganism or a mutant of said rosamicin-producing microorganism to provide a mutant microorganism that produces repromicin;

b) fermenting said mutant microorganism in an aqueous nutrient medium containing assimilable sources of carbon and nitrogen producing a fermentation broth; and c) recovering said repromicin from said fermentation broth.

17. The process of claim 16 wherein said rosamicin-producing microorganism is *Micromonospora rosaria* ATCC 29337 or ATCC 55708.

18. The process of claim 16 wherein said rosamicin-producing microorganism is *Micromonospora rosaria* ATCC 29337 or ATCC 55708.

19. A process for preparing repromicin comprising a) fermenting a mutant microorganism in an aqueous nutrient medium containing assimilable sources of carbon and nitrogen producing a fermentation broth; and b) recovering said repromicin from said fermentation broth.

20. The process of claim 19 wherein said mutant microorganism is a rosX mutant of *Micromonospora rosaria*.

21. The process according to claim 20 wherein said rosX mutant of *Micromonospora rosaria* is designated ATCC 55709.

22. A process for preparing an olefinic macrolide comprising a) mutating an epoxy macrolide producing microorganism to provide a mutant microorganism that produces a precursor to said epoxy macrolide consisting of said olefinic macrolide;

b) fermenting said mutant microorganism in an aqueous nutrient medium containing assimilable sources of carbon and nitrogen to form a fermentation broth; and c) recovering said olefinic macrolide from said fermentation broth.

* * * * *